US009040746B2

(12) United States Patent
Ball et al.

(10) Patent No.: US 9,040,746 B2
(45) Date of Patent: May 26, 2015

(54) SYSTEMS AND PROCESSES FOR THE PRODUCTION OF ISOPHTHALIC ACID AND TEREPHTHALIC ACID

(75) Inventors: George A. Ball, Hampstead, NC (US); Joseph G. Gentry, Houston, TX (US); Joseph P. Weller, Angleton, TX (US); Zhongyi Ding, Katy, TX (US); Weihua Jin, Katy, TX (US)

(73) Assignee: GTC Technology US, LLC, Houston, TX (US)

( * ) Notice: Subject to any disclaimer, the term of this patent is extended or adjusted under 35 U.S.C. 154(b) by 130 days.

(21) Appl. No.: 12/933,413

(22) PCT Filed: Mar. 18, 2009

(86) PCT No.: PCT/US2009/037514
§ 371 (c)(1),
(2), (4) Date: Oct. 27, 2010

(87) PCT Pub. No.: WO2009/117487
PCT Pub. Date: Sep. 24, 2009

(65) Prior Publication Data
US 2011/0057147 A1   Mar. 10, 2011

Related U.S. Application Data

(60) Provisional application No. 61/037,612, filed on Mar. 18, 2008.

(51) Int. Cl.
C07C 63/26 (2006.01)
C07C 51/265 (2006.01)
C07C 7/00 (2006.01)

(52) U.S. Cl.
CPC ............... *C07C 7/005* (2013.01); *C07C 51/265* (2013.01)

(58) Field of Classification Search
CPC ............................. C07C 51/265; C07C 63/26
See application file for complete search history.

(56) References Cited

U.S. PATENT DOCUMENTS

| 3,917,734 A | 11/1975 | deRosset |
| 4,185,073 A * | 1/1980 | Marsh et al. ................. 422/111 |
| 4,313,015 A * | 1/1982 | Broughton .................... 585/828 |
| 5,068,406 A | 11/1991 | Holzhauer et al. |
| 6,143,926 A * | 11/2000 | Parten .......................... 562/414 |
| 6,359,186 B1 | 3/2002 | Hotier et al. |
| 2005/0272951 A1 | 12/2005 | Noe' |

FOREIGN PATENT DOCUMENTS

| EP | 1489139 A1 | 12/2004 |
| GB | 748276 A | 4/1956 |
| GB | 787084 A | 12/1957 |
| GB | 837006 A | 6/1960 |
| KR | 10-1999-0031350 A | 5/1999 |

OTHER PUBLICATIONS

Machine Translation of Sang-Il Kim KR 1999-0031350.*

* cited by examiner

*Primary Examiner* — Rosalynd Keys
*Assistant Examiner* — Jennifer C Sawyer
(74) *Attorney, Agent, or Firm* — Winstead PC

(57) ABSTRACT

Various embodiments of the present invention generally disclose systems and processes for the conversion of a feed stream comprising at least one C8 aromatic into a product stream comprising isophthalic acid and purified terephthalic acid (IPA/TA).

4 Claims, 4 Drawing Sheets

SYSTEMS AND PROCESSES FOR THE PRODUCTION OF ISOPHTHALIC ACID AND TEREPHTHALIC ACID

BACKGROUND OF THE INVENTION

Background

Meta-xylene and Para-xylene are valuable chemical intermediates used in the production of isophthalic acid and terephthalic acid (IPA/TA (or CIPA/CTA)), purified or crude, used in the production of resins. Currently, there is much demand for resins that are used in the production of bottles. This market is expected to grow substantially in the coming years.

Meta-xylene may be derived from mixtures of $C_8$ aromatics separated from such raw materials as petroleum naphthas, particularly reformates, wherein the mixture of xylenes is usually made by fractional distillation or selective solvent extraction. The $C_8$ aromatics in such mixtures and their properties are:

|  | Freezing Point (° C.) | Boiling Point (° C.) | Density (Kg/m$_3$) |
| --- | --- | --- | --- |
| Ethylbenzene | −95.0 | 136.2 | 869.9 |
| Para-xylene | 13.2 | 138.5 | 863.9 |
| Meta-xylene | −47.4 | 138.8 | 866.3 |
| Ortho-xylene | −25.4 | 144.0 | 883.1 |

There are various sources of mixtures of $C_8$ aromatics. One such source is catalytically reformed naphthas and pyrolysis distillates. Other sources include but are not limited to alkylation, dealkylation or alkyl group transfer, such as TDP, toluene alkylation, transalkylation, and/or the like. The $C_8$ aromatic fractions from naphthas and pyrolysis distillates vary quite widely in composition and will usually be in the range of 10 wt % to 32 wt % ethylbenzene (EB) with the balance, xylenes, being divided approximately 50 wt % meta-xylene and 25 wt % each of para-xylene and ortho-xlyene.

The boiling point of ethylbenzene is very close to those of para-xylene and meta-xylene. Complete removal of ethylbenzene from the charge by conventional methods, e.g., distillation, is usually impractical due to cost factors. Ethylbenzene may be removed by other processes such as selective adsorption, like the process disclosed in U.S. Pat. No. 4,021,499; U.S. Pat. No. 4,079,094; U.S. Pat. No. 4,108,415; and, U.S. Pat. No. 4,497,972. Typically, ethylbenzene is converted catalytically in an isomerizer-separator loop.

In many processes for xylene isomerization, conversion of ethylbenzene is frustrated because at least a portion of the xylenes tend to also convert to other species. Thus, although catalytic removal of ethylbenzene is possible, operating conditions are still selected to balance the disadvantages of xylene loss by dealkylation or transalkylation with the conversion of ethylbenzene, thus depleting the available meta-xylene or para-xylene available to produce the corresponding isophthalic and/or teraphthalic acids (IPA and/or TA(CTA)). Accordingly, a need exists in the art for balanced systems and processes for the conversion of a feed stream comprising at least one $C_8$ aromatic into a product stream comprising isophthalic acid and terephthalic acid (IPA/TA).

SUMMARY OF THE INVENTION

Various embodiments of the present invention generally comprise systems and processes for the conversion of a feed stream comprising at least one $C_8$ aromatic into a product stream comprising isophthalic acid and terephthalic acid (IPA/TA). An embodiment of processes of the present invention discloses converting a feed stream comprising at least meta-xylene, para-xylene, and ethylbenzene, and optionally orth-xylene, into at least one product stream comprising isophthalic acid and terephthalic acid (IPA/TA), the process comprising the steps of:
  a. removing ethylbenzene from the feed stream to produce an ethylbenzene depleted feed stream;
  b. removing ortho-xylene from the ethylbenzene depleted feed stream to produce an ortho-xylene depleted feed stream;
  c. oxidizing the ortho-xylene depleted feed stream to produce the product stream, the product stream comprising IPA/TA in a proportion between about 0.5% and about 99.5% IPA and about 0.5% and about 99.5% TA.

Further embodiments of the present invention disclose a process for converting a feed stream comprising at least meta-xylene and para-xylene into at least one product stream comprising isophthalic acid and terephthalic acid (IPA/TA), the process comprising the step of:
  oxidizing the ortho-xylene depleted feed stream to produce the product stream, the product stream comprising IPA/TA in a proportion between about 0.5% and about 99.5% IPA and about 0.5% and about 99.5% TA Also disclosed are systems for the production of a product stream comprising isophthalic acid and terephthalic acid (IPA/TA) from a feed stream comprising at least meta-xylene and para-xylene, the system comprising:
  a. an ortho-xylene removal zone;
  b. a co-oxidation zone,
wherein the ortho-xylene removal zone is capable of removing components heavier than meta-xylene, and wherein the ortho-xylene removal zone is capable of producing an ortho-xylene depleted stream, and wherein the co-oxidation zone is capable of oxidizing both meta-xylene and para-xylene into crude isophthalic acid and crude terephthalic acid (C-IPA/C-TA).

BRIEF DESCRIPTION OF THE FIGURES

In order that the manner in which the above recited and other advantages and objects of the invention are obtained, a more particular description of the invention briefly described above will be rendered by reference to specific embodiments thereof, which are illustrated, in the appended drawings. Understanding that these drawings depict only typical embodiments of the invention and are therefore not to be considered limiting of its scope, the invention will be described with additional specificity and detail through the use of the accompanying drawings in which.

DETAILED DESCRIPTION OF THE INVENTION

The following definitions and explanations are meant and intended to be controlling in any future construction unless clearly and unambiguously modified in the following Description or when application of the meaning renders any construction meaningless or essentially meaningless. In cases where the construction of the term would render it meaningless or essentially meaningless, the definition should be taken from Webster's Dictionary, $3^{rd}$ Edition. Definitions and/or interpretations should not be incorporated from other patent applications, patents, or publications, related or not, unless specifically stated in this specification or if the incorporation is necessary for maintaining validity.

Exemplary, non-limiting embodiments and/or disclosures of process for the production of isophthalic acid and purified terephthalic acid include, but are not limited to, U.S. Pat. Nos. 7,285,684; 7,271,286; 6,562,997; 6,187,569; 6,461,840; 5,739,384; 5,068,406; 4,978,741; 4,855,492; and, 4,046,782, the contents of which are hereby incorporated by reference, as if they were presented herein in their entirety.

As used herein, a "fluid" is a continuous, amorphous substance whose molecules move freely past one another and that has the tendency to assume the shape of its container, for example, a liquid or a gas.

As used herein, "membrane apparatus" means and refers to flat sheet membranes, spiral wound flat sheet membranes, tubesheets, tubular tube membranes, hollow fiber membranes, and/or other membranes commonly used in industry.

As used herein, the term "mixed xylene" or "mixed xylenes" means and refers to an aromatic stream of hydrocarbons comprising about 20 to about 80 wt % meta-xylene, about 10 to about 60 wt % para-xylene, optionally about 10 to about 60 wt % ortho-xylene, and optionally about 0.1 to about 30 wt % ethylbenzene.

Other than in the operating examples, or where otherwise indicated, all numbers expressing quantities of components used herein are to be understood as modified in all instances by the term "about".

Figure 2:
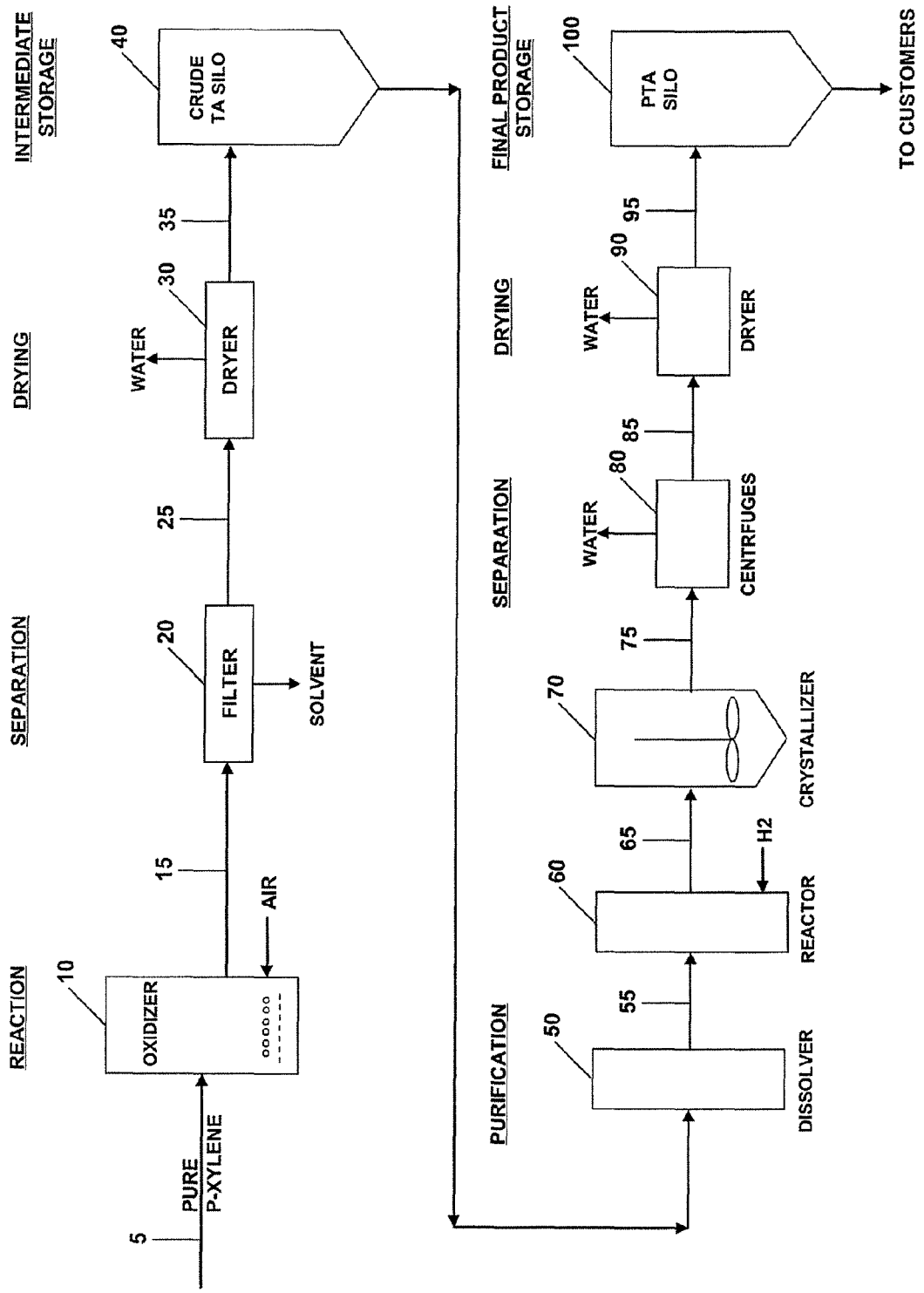
FIG. 2 is an illustration of a flow diagram showing a prior art system for the production of terephthalic acid (with the p-xylene feedstock) or isophthalic acid (if p-xylene feedstock were substituted by m-xylene feedstock).

Typically, various processes for producing Terephthalic Acid or Isophthalic Acid singularly are capable of being the same, or highly related, and can be accomplished with a system as is described in FIG. 2. Generally, the starting feedstock, after conversion, of para-xylene will yield terephthalic acid and the starting feed stock of meta-xylene will yield isophthalic acid.

In the embodiment of a prior art process or system for the production of Terephthalic Acid or Isophthalic Acid illustrated in FIG. 2, a xylene stream 5 is fed to an oxidizer 10. An oxygenated gas, typically air or pure oxygen, is fed into oxidizer 10 with a catalyst and solvent system. Stream 15 removed from oxidizer 10, an acid form of stream 5, is then separated, such as by a filter 20, wherein the catalysts and/or solvent can be recycled or removed/purged.

After separation, stream 35, comprising a crude acid of the xylene of stream 5, is fed to a dissolver, typically containing water or other solvent at an elevated temperature to aid dissolution. Optionally, stream 35 is capable of being stored in a silo 40 until needed for use or for other reactions as may be desired. Common products at this stage are either Crude Terephthalic Acid (CTA) or Crude Isophthalic Acid (C-IPA).

Stream 55 is then fed to a hydrogenation reactor system 60 to aid in removal of impurities from stream 55. Typically, impurities present in stream 55 react with the hydrogen and the impurity products formed are capable of being separated from the acid, such as by filter, sieve, centrifugation, cyclone separators and/or the like.

Stream 65 withdrawn from system 60 is then cooled and crystallized, such as in a crystallization system 70. Impurities are capable of being removed through at least one separation system 80. Separation system 80, if present, is capable of containing a variety of centrifuges, wash systems filters and or the like. The resulting product stream 95 is then dried in a dryer 90. Optionally, the contents of product stream 95 can be stored in a product silo 100. Common products at this stage are either Purified Terephthalic Acid (PTA) or Pure Isophthalic Acid (IPA). Heretofore, however, PTA and IPA have not been produced in a useable product stream together.

Accordingly, in general, various embodiments of the present invention comprise a process and/or system for converting a feed stream comprising at least meta-xylene, para-xylene, and ethylbenzene, and optionally ortho-xylene, into at least one product stream comprising isophthalic acid and terephthalic acid (IPA/TA), the process comprising the steps of a. removing ethylbenzene from the feed stream to produce an ethylbenzene depleted feed stream;

b. removing ortho-xylene from the ethylbenzene depleted feed stream to produce an ortho-xylene depleted feed stream;

c. oxidizing the ortho-xylene depleted feed stream to produce the product stream, the product stream comprising IPA/TA in a proportion between about 0.5% and about 99.5% IPA and about 0.5% and about 99.5% TA.

In an alternate embodiment, the product stream comprising IPA/TA is produced in a proportion between about 0.2% and about 10.0% IPA and about 90% and about 99.8% TA. In yet an alternate embodiment, the product stream comprising IPA/TA is produced in a proportion between about 0.1% and about 25.0% IPA and about 75% and about 99.9% TA. In an alternate embodiment, the product stream comprising IPA/TA is produced in a proportion between about 0.1% and about 99.9% IPA and about 1.0% and about 99.9% TA. In general, an embodiment of a process of the present invention can be modified to produce IPA/TA in any desired proportion.

In general, the feed stream comprises from about 1 wt % to about 40 wt % ethylbenzene, from about 20 wt % to about 80 wt % meta-xylene, from about 5 wt % to about 30 wt % ortho-xylene, and from about 0.5 wt % to about 40 wt % para-xylene. In an alternate, the hydrocarbon feed stream comprises from about 1 wt % to about 20 wt % ethylbenzene, from about 50 wt % to about 65 wt % meta-xylene, from about 20 wt % to about 30 wt % ortho-xylene, and from about 0.5 wt % to about 5 wt % para-xylene. In an alternate, the hydrocarbon feed stream comprises from about 0.1 wt % to about 50 wt % ethylbenzene, from about 0.1 wt % to about 99.9 wt % meta-xylene, from about 0.1 wt % to about 99.9 wt % ortho-xylene, and from about 0.1 wt % to about 99.9 wt % para-xylene. In alternate embodiment, the feed stream comprises a mixed xylene feed stream comprising about 20% ethyl benzene, about 20% ortho-xylene, about 40% meta-xylene, and about 20% para-xylene.

The production of IPA and/or TA has many uses. A very popular use is the production of IPA and TA based polymers and resins. A very common example is the use of IPA and PTA based polymers to produce polyester bottles.

Figure 1:
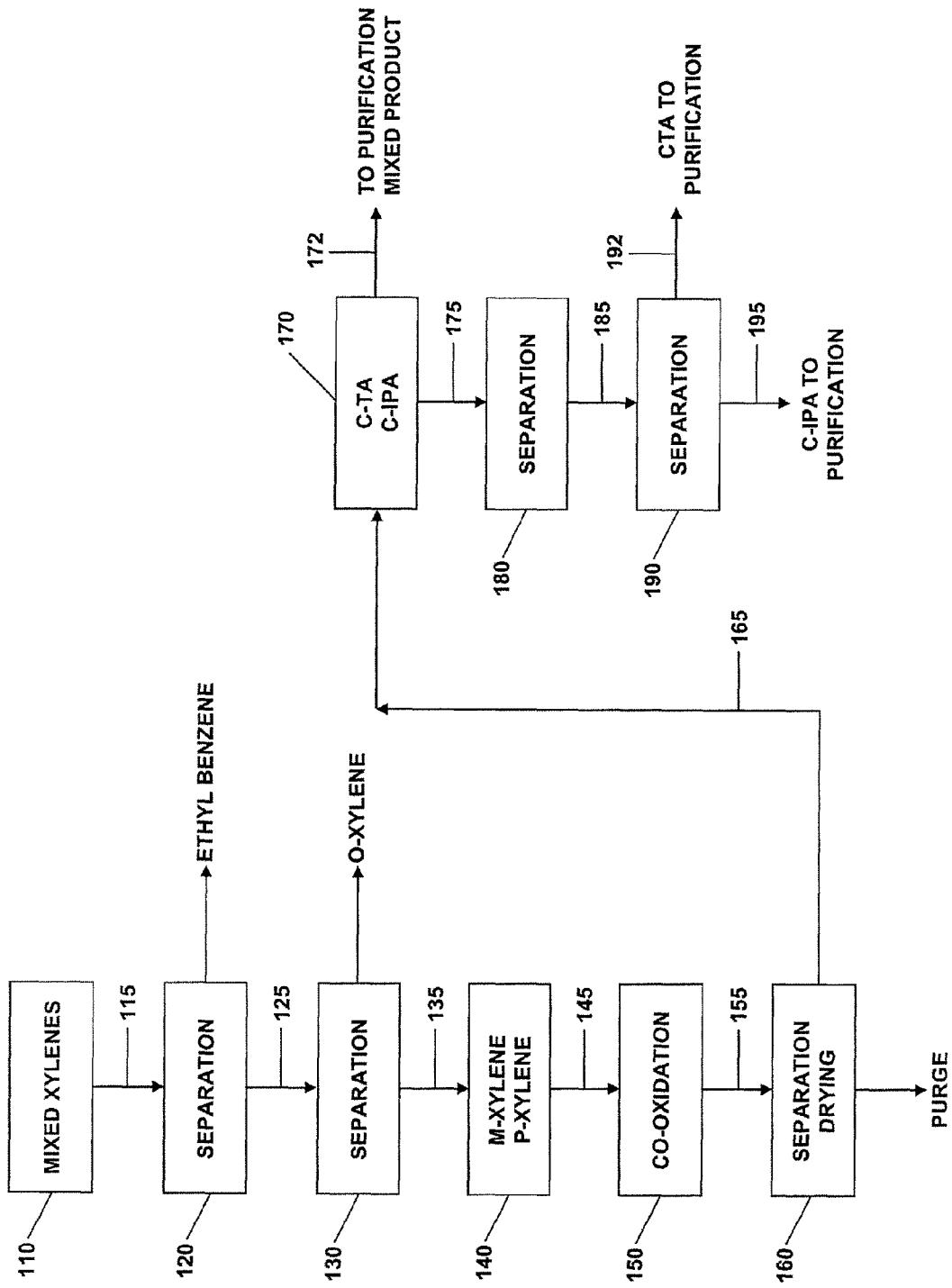
FIG. 1 is an illustration of an embodiment of a flow diagram showing an embodiment of a process of the present invention.

Referring now to FIG. 1, an embodiment of a base flow diagram depicting generalized process steps is disclosed. In general, various embodiments of the present invention, depending upon the feed stream conditions, comprise the steps of obtaining a stream 115 of a mixture of xylenes 110, such as a mixed xylenes stream;

removing ethyl benzene 120 from the stream of the mixture of xylenes 115 to produce an ethylbenzene depleted stream 125;

removing ortho-xylene 130 and heavier components from the mixture of xylenes 115 to obtain a stream comprising meta-xylene and para-xylene 135;

optionally adding excess para-xylene and/or meta-xylene (not shown);

co-oxidizing 150 the stream comprising meta-xylene and para-xylene 145 wherein the resulting stream comprises the acids of the meta-xylene and the para-xylene 155;

separating/drying 160 the resulting stream 155;

optionally purifying 170 the resulting stream 165 to produce a product stream 172 comprising isophthalic acid and terephthalic acid (IPA/TA);

optionally dissolving 180 stream 175 wherein IPA and TA are placed in solution;

optionally removing 190 stream 185 to produce a stream 192 comprising TA and/or a stream 195 comprising IPA.

Various other operational arrangements exist and would be understood by one of ordinary skill in the art, such as, but not limited to arranging the ortho-xylene removal zone before the ethyl benzene removal zone, or, using a single zone for the removal of ortho-xylene and ethyl benzene.

Prior to oxidizing the feed stream comprising para-xylene and meta-xylene, various embodiments of the present invention contemplate adjusting the proportion of IP/TA by adding excess para-xylene or excess meta-xylene to the ortho-benzene depleted feed stream. The excess para-xylene and/or meta-xylene will enable the process to be adjusted and result in the production of more of either IPA or TA after oxidation, thereby enabling the ratios to be adjusted as required by a polymer producer.

Generally, any solvent will work with various embodiments of the present invention, as would be appreciated by one of ordinary skill in the art. A non-exclusive list of solvents for use in oxidation include acetic acid, water, other acids, and/or the like. Likewise, generally, all catalysts useful for oxidation are capable of use with various embodiments of the present invention. A non-exclusive list of catalysts include Cobalt, Manganese. Bromine, Fluorine, and/or the like.

After oxidation, the meta-xylene and para-xylene stream will contain catalyst and solvent that must be removed, such as by a filter and a dryer. The catalyst is separated from the product stream and can be recycled or discarded. The solvent collected can be recycled or passed off as waste. Various dryers and/or filters are capable of performing the separating and/or drying. At this point, the product stream comprises a crude, or not purified, product stream comprising C-TA and C-IPA.

The C-TA and C-IPA can be further processed to produce a product stream comprising purified TA and purified IPA. In an embodiment, the crude IPA/TA is re-dissolved in a solvent, separated and/or dried to produce a purified stream comprising IPA/TA or pure IPA/PTA. In further embodiments, the purified IPA and PTA can be separated, if desired, into separate products.

Also disclosed herein are systems for the production of a product stream comprising isophthalic acid and terephthalic acid (IPA/TA) from a feed stream comprising at least meta-xylene and para-xylene, optionally ethylbenzene, and optionally ortho-xylene, the system comprising:

a. an ortho-xylene removal zone;

b. a co-oxidation zone, wherein the ortho-xylene removal zone is capable of removing components heavier than meta-xylene and para-xylene, and wherein the ortho-xylene removal zone is capable of producing an ortho-xylene depleted stream, and wherein the co-oxidation zone is capable of oxidizing both meta-xylene and para-xylene into crude isophthalic acid and crude terephthalic acid (C-IPA/C-TA). Further embodiments comprise an ethylbenzene removal zone for removing ethylbenzene. Further embodiments comprise a purifying zone capable of removing impurities from the C-IPA/C-TA) whereby purified IPA and Purified TA is produced.

Structures and modalities for the ethylbenzene removal zone, the ortho-xylene removal zone, the co-oxidation zone, the purifying zone, and the like can be any structure common in the art, such as distillation or separation columns, dryers, drums, beds, catalyst beds, pressure, temperature variation, adsorption beds, crystallizers, and/or the like.

Various embodiments of the present invention are capable of producing acids that can be converted into a polymer, such as a polyester polymer. Polyester polymers are used in the production of various items, including, but not limited to a bottle, a film, a fiber, or an injection molded article.

In yet a further embodiment, a process for converting a feed stream comprising at least meta-xylene and para-xylene into at least one product stream comprising isophthalic acid and terephthalic acid (IPA/TA) is disclosed, the process comprising the steps of:

a. removing ortho-xylene from the feed stream to produce an ortho-xylene depleted feed stream, and b. oxidizing the ortho-xylene depleted feed stream to produce a product stream, the product stream comprising IPA/TA in a proportion between 0.5% and about 99.5% IPA and about 0.5% and about 99.5% TA.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope. Further, all published documents, patents, and applications mentioned herein are hereby incorporated by reference, as if presented in their entirety.

Examples:

Feedstock

In general, any aromatic $C_8$ mixture containing ethylbenzene and a xylene may be used as feed to the process of this invention. In general, the feed stream comprises from about 1 wt % to about 25 wt % ethylbenzene, from about 20 wt % to about 80 wt % meta-xylene, from about 5 wt % to about 30 wt % ortho-xylene, and from about 0.5 wt % to about 20 wt % para-xylene. In an alternate, the hydrocarbon feed stream comprises from about 1 wt % to about 20 wt % ethylbenzene, from about 50 wt % to about 65 wt % meta-xylene, from about 20 wt % to about 30 wt % ortho-xylene, and from about 0.5 wt % to about 5 wt % para-xylene. In alternate embodiment, the feed stream comprises a mixed xylene feed stream comprising about 20% ethyl benzene, about 20% ortho-xylene, about 40% meta-xylene, and about 20% para-xylene.

Process

Figure 3:
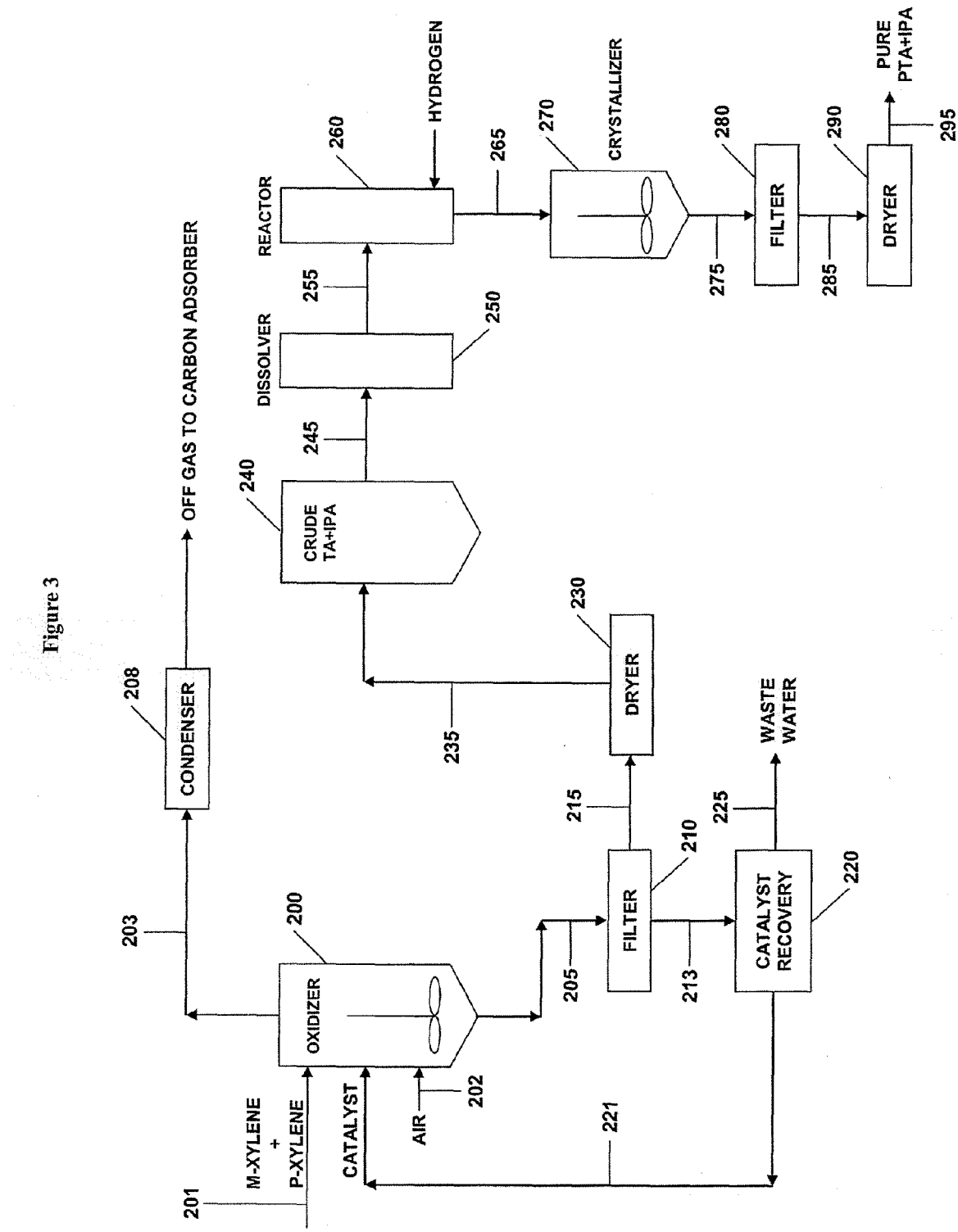
FIG. 3 is an illustration of an alternate embodiment of a system of the present invention.

Now referring to FIG. 3, an embodiment of a system for performing a process of the present invention is disclosed. In general, a feed stream 201 comprising a feed of meta-xylene and para-xylene is fed into an oxidizer 200. In this exemplary embodiment, it is contemplated that ethylbenzene plus toluene, and heavier components such as ortho-xylene have already been removed and/or minimized. Oxidizer 200 contains at least one of a solvent and a catalyst with an oxygenated gas or air being fed in as stream 202. The feed remains in oxidizer 200 for a period of time sufficient to effect oxidation of the xylenes to the respective acidic foiin, i.e., the para-xylene to TA and meta-xylene to IPA.

An overhead or off gas from an upper portion of oxidizer 200 is capable of being removed as stream 202 wherein the off gas can be treated such as through a condenser 208 and/or other unit such that the release of off gas, other than through an environmentally controlled manner, is reduced or eliminated.

After oxidizing, a stream 205 comprising oxidized feed stream 201, catalyst, and solvent is removed as stream 205. A separation apparatus, such as filter 210, is used to remove catalyst and/or solvent from stream 205 resulting in a stream 215. Recovered catalysts is collected in a recovery unit 220 and reprocessed in stream 221 into oxidizer 200.

Stream 215 is then dried in dryer 230 to eliminate residual moisture and/or solvent. Dried crude TA and IPA (Crude Product) is then withdrawn as stream 235 and passed into a storage tank 240.

When a purified TA and IPA is desired, Crude Product is withdrawn as stream 245 and fed to dissolver 250 which may use various solvents, heat, and/or pressure to effect dissolution of the Crude Product, as is common in the art.

The crude acid is fed as stream 255 to a hydrogenation reactor 260, where the impurities are reacted with hydrogen and the products formed are able to be separated from the acid. The resulting stream 265 is then crystallized in a series of crystallizers 270 and then fed as stream 275 to a separation device 280. A stream 285 is then dried in dryer 290 wherein a mixture of Pure Terephthalic and Isophthalic acid is withdrawn as a stream 295.

A mixed xylene feed stream comprising about 20% ethyl benzene, about 20% ortho-xylene, about 40% meta-xylene, and about 20% para-xylene, after conversion according to a process of the present invention, has been projected to produce Isophthalic acid and Terephthalic in a ratio of approximately 2:1. In various other embodiments, the xylene feed stream is in a ratio of about 0.1 to about 10.0:about 0.5 to about 10.0. In an alternate embodiment, the xylene feed stream is in a ratio of about 1.0 to about 5.0:about 1.0 to about 5.0.

Figure 4:
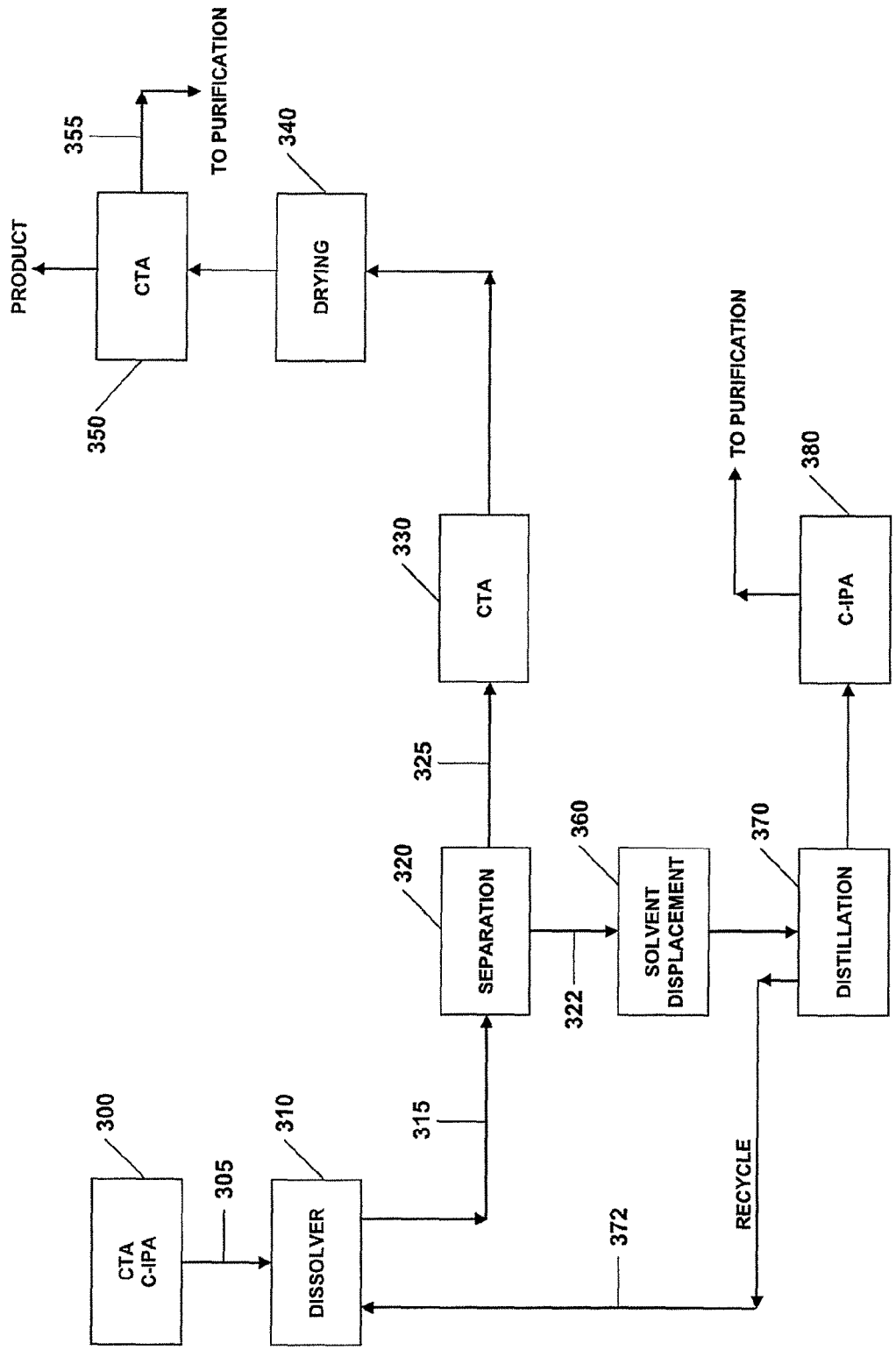
FIG. 4 is an illustration of an alternate embodiment of a system of the present invention.

A process for removing a mixture of crude TA and IPA is illustrated in FIG. 4. Generally, storage tank or silo 300 containing a mixture of CTA and C-IPA is fed as stream 305 to a dissolver 310 which contains acids and/or other solvents capable of dissolving CTA and C—IPA. Stream 315 withdrawn from the dissolver is fed to removal zone 320 where the material is selectively crystallized, filtered, centrifuged, and/ or the like, wherein CTA is separated out in stream 325 as CTA which can be dried in a dryer 340 and produced as a product 350 or be subject to further purification.

Stream 322 comprises a C-IPA and solvent. A solvent displacement system 360, such as a column 370, is used to aid in removing the solvent from the C-IPA. Stream 372 comprising recovered solvent is fed back into dissolver 310 and a C-IPA product 380 is produced which may be subject to further purification.

Process Conditions

In accordance with the present invention, the above described feedstock may be contacted with the catalyst system under suitable conversion conditions to effect hydrogenation. Examples of these conversion conditions include a temperature of from about 200° C. to about 550° C., a pressure of from 0 psig to about 1,000 psig, a WHSV of between about 0.1 hr$^{-1}$ and about 200$^{-1}$, and an H$_2$/HC molar ratio of between about 0.2 and about 10. An alternative to these conversion conditions may include a temperature of from about 325° C. to about 475° C., a pressure of from about 50 psig to about 400 psig, a WHSV of between about 3 hr$^{-1}$ and about 50 hr$^{-1}$, and a H$_2$/HC molar ratio of between about 1 and about 5. The WHSV is based on the weight of catalyst composition, i.e., the total weight of active catalyst and, if used, a binder.

Oxidation

In various embodiments, the oxidation of the xylenes to CTA and C-IPA takes place in a agitated reactor in which air is injected through nozzles. A mixture of xylenes, solvent such as acetic acid, and catalyst is fed to the reactor. The air feed rate is controlled according to the O$_2$ content in the reactor off-gas which is monitored and recorded by dedicated process gas analyzers. The reaction temperature is about 200° C. and the pressure is about 1.6 MPa. Heat generated by the oxidation reactor is removed by the vaporization of solvent and reaction water.

Catalyst

The form and the particle size of the catalyst are not critical to the present invention and may vary depending, for example, on the type of reaction system employed. Non-limiting examples of the shapes of the catalyst in the present invention include balls, pebbles, spheres, extrudates, channeled monoliths, honeycombed monoliths, microspheres, pellets, or structural shapes, such as lobes, trilobes, quadralobes, pills, cakes, honeycombs, powders, granules, and the like, fainted using conventional methods, such as extrusion or spray drying.

In general, the catalyst may be soluble in the reaction medium comprising solvent and the aromatic carboxylic acid precursor(s) or, alternatively, a heterogeneous catalyst may be used. The catalyst, whether homogeneous or heterogeneous, typically comprises one or more heavy metal compounds, e.g. cobalt and/or manganese compounds, and may optionally include a hydrogenation promoter. In an embodiment, the catalyst is palladium.

Where the catalyst is in heterogeneous form, it may be suitably located within the reaction zone so as to secure contact between the continuously flowing reaction medium and the catalyst. In this event, the catalyst may be suitably supported and/or constrained within the reaction zone to secure such contact without unduly constricting the flow cross-section. For instance, the heterogeneous catalyst may be coated on or otherwise applied to, or embodied in, static elements (e.g. elements forming an openwork structure) positioned of within the reaction zone so that the reaction medium flows over the same. Such static elements may additionally serve to enhance mixing of the reactants as they pass through the reaction zone. Alternatively the catalyst may be in the form of mobile pellets, particles, finely divided form, metal sponge form or the like with means being provided if necessary to confine the same to the reaction zone so that, in operation, the catalyst pellets etc become suspended or immersed in the reaction medium flowing through the reaction zone. The use of a heterogeneous catalyst in any of these ways confers the advantage of being able to confine the catalysis effect to a well-defined zone so that, once the reaction medium has traversed the zone, further hydrogenation takes place at a reduced rate or may be significantly suppressed.

A support for the hydrogenation catalyst can be less catalytically active or even inert to the hydrogenation reaction. The support may be porous and typically has a surface area, including the area of the pores on the surface, of at least 15 m$_2$/gm to 500 m$_2$/gm, e.g. from 50 m$_2$/gm to 200 m$_2$/gm, with a surface area of about 80 m$_2$/gm to about 150 m$_2$/gm being preferred. The catalyst support materials should be substantially corrosion resistant and substantially oxidation resistant under the conditions prevailing. The support component of the oxidation catalyst may be pure or a composite of materials, the latter being employed for example to impart desired chemical or physical characteristics to the catalyst. In an embodiment, the catalyst support material comprises zirconium dioxide. In an alternate embodiment, the support is carbon. In general, any catalyst will function with various embodiments of the present invention

What is claimed is:

1. A process for converting a feed stream comprising at least ortho-xylene, meta-xylene, para-xylene, and ethylbenzene into at least one product stream comprising isophthalic acid and terephthalic acid (IPA/TA), said process comprising the steps of:
   a. providing said feed stream comprising 1 to 25 wt % ethylbenzene, 20 to 80 wt % meta-xylene, 5 to 30 wt % ortho-xylene and 0.5 to 20 wt % para-xylene;
   b. removing ethylbenzene from said feed stream to produce an ethylbenzene depleted feed stream by using selective adsorption onto a molecular sieve type of media;
   c. removing ortho-xylene from said ethylbenzene depleted feed stream to produce an ortho-xylene and ethylbenzene depleted feed stream containing meta-xylene and para-xylene;
   d. oxidizing said ortho-xylene and ethylbenzene depleted feed stream to produce a product stream, said product stream comprising IPA/TA in a ratio of 1:5 to 5:1, wherein the oxidizing step is carried out using a catalyst that is selected from the group consisting of cobalt, manganese and palladium and includes a hydrogenation promoter and is carried out at a temperature ranging from 200° C. to 550° C., a pressure ranging from 0 psig to 1000 psig, a WHSV of between 0.1 hr$^{-1}$ to 200 hr$^{-1}$ and a hydrogen/hydrocarbon molar ratio of between 1 and 5;
   e. drying said product stream in a dryer to remove residual solvent and water;
   f. removing a substantially purified IPA/TA product stream;
   g. dissolving said product stream; and
   h. separating said IPA and said TA from said dissolved product stream.

2. The process of claim 1, further comprising adding one of either para-xylene or meta-xylene to said ethylbenzene depleted and ortho-xylene depleted feed stream.

3. The process of claim 1, wherein said feed stream comprises a mixed xylene feed stream comprising about 20% ethyl benzene, about 20% ortho-xylene, about 40% meta-xylene, and about 20% para-xylene.

4. The process of claim 3, wherein said feed stream comes from at least one of a catalytic reforming unit or process, a steam cracking unit or process, a coking unit or process, a pyrolysis oil unit or process, an aromatics alkylation unit or process, or transalkylation.

* * * * *